United States Patent [19]

Waldner

[11] Patent Number: 4,923,993
[45] Date of Patent: * May 8, 1990

[54] PROCESS FOR THE PREPARATION OF 2-PYRIDINECARBOXYLIC ACID DERIVATIVES AND 1-AMINO-1,4-DIHYDROPYRIDINE-2-CARBOXYLIC ACID DERIVATIVES

[75] Inventor: Adrian Waldner, Allschwil, Switzerland

[73] Assignee: Ciba-Geigy Corporation, Ardsley, N.Y.

[*] Notice: The portion of the term of this patent subsequent to May 31, 2005 has been disclaimed.

[21] Appl. No.: 240,165

[22] Filed: Sep. 2, 1988

Related U.S. Application Data

[63] Continuation of Ser. No. 919,532, Oct. 16, 1986, abandoned.

[30] Foreign Application Priority Data

Oct. 25, 1985 [CH] Switzerland .................. 4609/85

[51] Int. Cl.$^5$ ............... C07D 213/803; C07D 471/04; C07D 491/048
[52] U.S. Cl. .................. 546/250; 546/193; 546/194; 546/281; 546/286; 544/124
[58] Field of Search ............ 546/250, 286, 193, 194, 546/281; 544/124

[56] References Cited

U.S. PATENT DOCUMENTS 2,494,204  1/1950  Robinson et al. ............... 546/250
4,748,244  5/1988  Waldner et al. ............... 544/313

FOREIGN PATENT DOCUMENTS 185621  6/1986  European Pat. Off. ............ 546/300

OTHER PUBLICATIONS

E. Schrötter et al; Pharmazie 39(1984), 155–158.
B. Serckx-Poncin et al; Tetrahedron Letters, (1982), (No. 23), 3261.
Houben-Weyl, Methoden der Organischen Chemie, Thieme Stuttgart, 1952, vol. 8, p. 663.
L. N. Yakhatua et al., Chem. Het. Comp, 1967, 829–31.
Y. Tamura et al; Synthesis 1984, 930–3.
K. T. Potts et al; J. Chem. Soc. 1984, 114–6.

Primary Examiner—Alan L. Rotman
Attorney, Agent, or Firm—Kevin T. Mansfield

[57] ABSTRACT

The process of the invention relates to the reaction of hydrazones of formula II

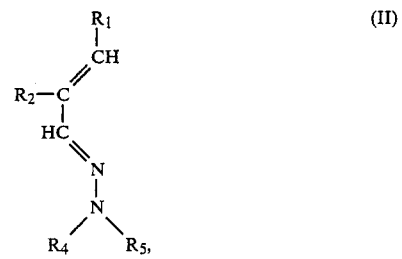

with α-chloro- or α-bromoarylonitrile or α-chloro- or α-bromoacrylates of formula III

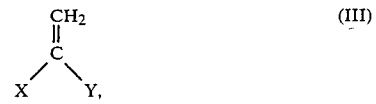

to 1-amino-2-cyano-1,4-dihydropyridines or 1-amino-1,4-dihydropyridine-2-carboxylic acid esters of formula IV

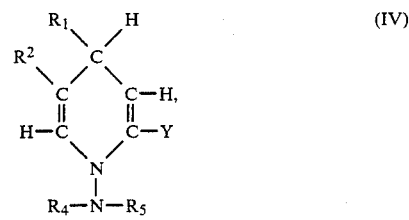

which are converted into pyridine derivatives of formula I

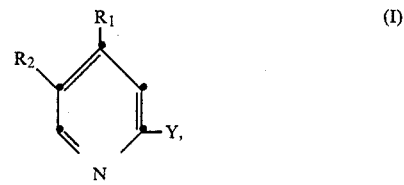

by treatment with an acid, with removal of $R_4R_5NH$. Y is —CN or —$COOR_3$ and $R_1$ to $R_5$ may be alkyl.

12 Claims, No Drawings

PROCESS FOR THE PREPARATION OF 2-PYRIDINECARBOXYLIC ACID DERIVATIVES AND 1-AMINO-1,4-DIHYDROPYRIDINE-2-CARBOXYLIC ACID DERIVATIVES

This is a continuation of application Ser. No. 919,532 filed Oct. 16, 1986, abandoned.

The present invention relates to a Diels-Alder reaction in which an unsaturated hydrazone is reacted with an α-haloacrylonitrile or α-haloacrylate to a 1-amino-2-cyano-1,4-dihydropyridine or 1-amino-1,4-dihydropyridine-2-carboxylic acid ester, which is converted into the corresponding pyridine derivative by treatment with an acid.

The Diels-Alder reaction of 1-amino-1-aza-3-methyl-1,3-butadiene with acrylonitrile or methacrylate to give 1-amino-3-methyl-2-cyano- or -2-carbomethoxy-1,2,3,4-tetrahydropyridine is described in Tetrahedron Letters, Vol. 23, No. 32, pp. 3261–3264 (1982). The removal of the amino group under reductive conditions leads to piperidine derivatives, but not to pyridine derivatives. It is the object of the present invention to provide a process by means of which it is possible to prepare regiospecifically substituted 2-cyanopyridines or 2-pyridinecarboxylic acid esters in good yields from cheap and readily accessible starting materials Specifically, the present invention relates to a process for the preparation of 2-cyanopyridines or 2-pyridinecarboxylic acid esters of formula I

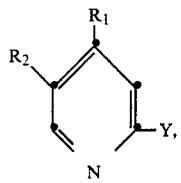

wherein $R_1$ is hydrogen, an unsubstituted or substituted linear or branched alkyl, alkylthio or alkoxy group; an unsubstituted or substituted phenyl or phenoxy group; $R_2$ independently has the same meaning as $R_1$ and is additionally fluorine, chlorine or bromine; or $R_1$ and $R_2$ together are a substituted or unsubstituted $C_3$–$C_4$alkylene bridge and Y is CN or $COOR_3$, wherein $R_3$ is alkyl, cycloalkyl, aryl or aralkyl, which process comprises (a) reacting a hydrazone of formula II

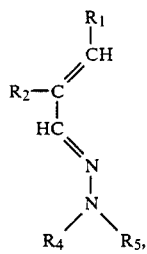

wherein $R_1$ and $R_2$ are as defined for formula I and $R_3$ and $R_4$ are each individually alkyl, cycloalkyl, aralkyl or aryl or, when taken together, are alkylene or oxaalkylene, in the presence of an inert solvent and a base, with α-chloro- or α-bromoacrylonitrile or α-chloro- or α-bromoacrylate of formula II

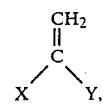

wherein X is halogen and Y is as defined for formula I, to give a 1-amino-2-cyano-1,4-dihydropyridine or 1-amino-1,4-dihydropyridine-2-carboxylic acid ester of formula IV

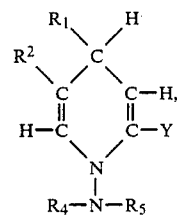

wherein $R_1$, $R_2$, $R_4$, $R_5$ and Y have the given meanings, and (b) converting the 1-amino-2-cyano-1,4-dihydropyridine or 1-amino-1,4-dihydropyridine-2-carboxylic acid ester of formula IV into a 2-cyanopyridine or 2-pyridinecarboxylic acid ester of formula I by treatment with an acid, with removal of $HNR_4R_5$.

Halogen is fluorine, chlorine, bromine or iodine. X in formula II is preferably chlorine or bromine.

In the above formulae, $R_1$ and $R_2$ as alkyl, alkylthio and alkoxy preferably contain 1 to 6 carbon atoms. Examples of suitable substituents of these radicals are halogen, preferably fluorine, chlorine and bromine, $C_1$–$C_4$alkoxy, phenyl, phenoxy, cyano and $C_1$–$C_4$-alkoxycarbonyl. Preferred substituents are halogen atoms. Examples of such radicals are: methyl, ethyl, n-propyl, isopropyl, n-butyl, tert-butyl, 1-pentyl, 3-pentyl, 1-hexyl, 2-hexyl, 3-hexyl, methoxy, ethoxy, n-propoxy, isopropoxy, n-butoxy, tert-butoxy, methylthio, ethylthio, propylthio, butylthio, hydroxymethyl, fluoromethyl, trifluoromethyl, 2-cyanoethyl, 2-chloroethyl, bromomethyl, benzyl, chlorobenzyl, methoxymethyl, ethoxymethyl, and methoxyethyl.

Examples of suitable substituents of $R_1$ and $R_2$ as phenyl and phenoxy are halogen such as fluorine, chlorine and bromine, cyano, $C_1$–$C_4$alkyl, $C_1$–$C_4$alkoxy, $C_1$–$C_4$haloalkyl or $C_1$–$C_4$cyanoalkyl. Examples of such radicals are: methylphenyl, ethylphenyl, methoxyphenyl, ethoxyphenyl, chlorophenyl, fluorophenyl, difluorophenyl, bromophenyl, chlorophenoxy, methylphenoxy, methoxyphenoxy, fluoromethylphenyl difluoromethylphenyl, trifluoromethylphenyl, chloromethylphenyl, cyanomethylphenyl, 2-cyanoethylphenyl, trifluoromethylphenoxy and cyanomethylphenoxy.

In a preferred embodiment of the invention, $R_1$ is hydrogen. $R_2$ is preferably $C_1$–$C_6$alkyl, $C_1$–$C_6$alkoxy or $C_1$–$C_6$alkylthio, the alkyl moiety of which may be mono- or perhalogenated.

$R_3$ as alkyl may be linear or branched and contains preferably 1 to 6 carbon atoms. $R_3$ as cycloalkyl is preferably cyclopentyl or cyclohexyl. $R_3$ as aryl or aralkyl is preferably phenyl or benzyl, each of which may be substituted by e.g. $C_1$–$C_4$alkyl, $C_1$–$C_4$alkoxy or halogen such as fluorine, chlorine or bromine.

$R_4$ and $R_5$ as alkyl may be linear or branched and contain preferably 1 to 6, most preferably 1 to 4, carbon atoms. Especially preferred radicals $R_4$ and $R_5$ are ethyl or methyl. $R_4$ and $R_5$ as cycloalkyl are preferably cyclopentyl or cyclohexyl. $R_4$ and $R_5$ as aryl are preferably phenyl and, as aralkyl, are preferably phenylalkyl containing 1 to 4 carbon atoms in the alkyl moiety and are most preferably benzyl.

$R_4$ and $R_5$ together as alkylene are preferably tetramethylene or pentamethylene and, as oxaalkylene, are 3-oxapentylene.

$R_1$ and $R_2$ together as $C_3$–$C_4$alkylene are preferably tetramethylene. The trimethylene or tetramethylene group so formed may be substituted by more than one substituent selected from the group consisting of halogen, alkoxy, alkylthio, cyano, haloalkyl, haloalkoxy and haloalkylthio.

Suitable solvents for carrying out the process of this invention [reaction step (a)] are those which are inert to the reactants, e.g. polar, aprotic solvents which may be used singly or as mixtures of at least two such solvents. Examples are: ethers such as dibutyl ether, tetrahydrofuran, dioxane, dimethyl ethylene glycol, diethyl diethylene glycol, dimethyl triethylene glycol; halogenated hydrocarbons such as methylene chloride, chloroform, 1,2-dichloroethane, 1,1,1-trichloroethane, 1,1,2,2-tetrachloroethane; carboxylic acid esters and lactones such as ethyl acetate, methyl propionate, ethyl benzoate, 2-methoxyethyl acetate, γ-butyrolactone, o-valerolactone and pivalolactone; carboxamides and lactams such as formamide, acetamide, N-methylformamide, N,N-dimethylformamide, N,N-diethylformamide, N,N-dimethylacetamide, N,N-diethylacetamide, γ-butyrolactam, ε-caprolactam, N-methylpyrrolidone, N-acetylpyrrolidone, N-methylcaprolactam, tetramethylurea, hexamethylphosphoric triamide; sulfoxides such as dimethylsulfoxide; sulfones such as dimethyl sulfone, trimethylene sulfone, tetramethylene sulfone; tertiary amines such as trimethylamine, triethylamine, N-methylpyrrolidone, N-methylpiperidine, N-methylmorpholine; substituted benzenes such as chlorobenzene, nitrobenzene; and nitriles such as acetonitrile. The above mentioned solvents can also be used in reaction step (b).

The compounds of formulae II and III are known or can be prepared by known methods. They are preferably employed in equimolar amounts. However, a small excess of unsaturated hydrazones of formula II may be employed.

The reaction temperature in the first step is preferably not less than 40° C., most preferably in the range from 40° to 100° C. Preferred bases are especially those which are soluble in the solvent employed. Examples of suitable bases are alkali metal carbonates such as lithium, sodium or potassium carbonate and, in particular, organic amines, preferably tertiary amines which may simultaneously act as solvent. Preferred tertiary amines are those containing $C_1$–$C_4$alkyl moieties, e.g. triethylamine.

In an advantageous embodiment of the process of this invention, the hydrazone of formula II and the base are dissolved in the solvent and the solution is slowly added to the heated solution of the compound of formula III.

The 1-amino-1,4-dihydropyridine derivatives of formula IV can be used as crude product or isolated before the second reaction step. When carrying out reaction step (a), the desired compound of formula I can be formed partially. The treatment with an acid is preferably effected at room temperature. Suitable acids are in particular mineral acids, e.g. hydrohalic acids (hydrochloric acid, hydrobromic acid, hydroiodic acid), perchloric acid or sulfuric acid. It is preferred to use a solution of hydrogen chloride, hydrogen bromide or hydrogen iodide in an organic solvent, with hydrogen chloride being most preferred.

The isolation and purification of the compounds prepared by the process of the invention is effected by conventional methods such as filtration, extraction, distillation, crystallisation or chromatographic methods.

The invention further relates to 1-amino-2-cyanodihydropyridines and 1-amino-dihydropyridine-2-carboxylic acid esters of formula IV

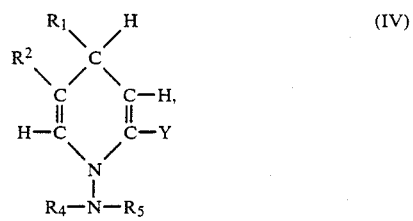

wherein $R_1$ is hydrogen, an unsubstituted or substituted linear or branched alkyl, alkylthio or alkoxy group, a substituted or unsubstituted phenyl or phenoxy group, $R_2$ independently has the same meaning as $R_1$ and is additionally fluorine, chlorine or bromine, or $R_1$ and $R_2$, when taken together, are a substituted or unsubstituted $C_3$–$C_4$alkylene bridge, and Y is CN or COOR$_3$, wherein $R_3$ is alkyl, cycloalkyl, aryl or aralkyl, and $R_4$ and $R_5$ are each individually alkyl, cycloalkyl, aralkyl or aryl or together are alkylene or oxaalkylene. The preferred meanings of $R_1$, $R_2$, $R_3$, $R_4$, $R_5$ and Y are the same as those indicated above.

The pyridine derivatives of formula I are obtained by the process of this invention in high yield from readily accessible and cheap starting materials. The synthesis is easy to perform and is regiospecific.

The compounds of formula I can be used as pharmaceuticals, for example as fusaric acid [q.v. Pharmazie 39, Vol. 3, page 155 (1984)]. They are also useful intermediates for agrochemicals, e.g. after substitution of the nitrile group (via amide, amine) by a halogen group.

Thus, for example, the 2-chloro-5-haloalkylpyridines known from European patent application EP-A 0 185 621, e.g. 2-chloro-5-pentachloroethylpyridine VIII, can be prepared starting from 2-cyanoethylpyridine of formula I ($R_1$=H, $R_2$=$C_2H_5$, Y=CN) in accordance with the following reaction scheme:

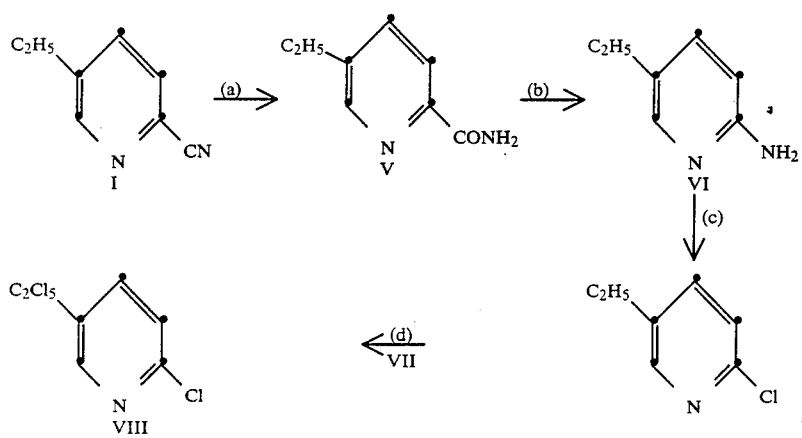

The individual process steps (a) to (d) can be carried out by methods analogous to those known from the literature (Houben-Weyl, Methoden der Organischen Chemie, Thieme, Stuttgart 1952, Vol. 8, p. 663; L. N. Yakhoutov et al., Khim. Geterotsikl-Soedin 1967, 1063–7; EP-A 0 186 621).

The invention is illustrated by the following Examples.

EXAMPLE 1

Preparation of 5-ethyl-2-cyanopyridine 39.3 g of 1-dimethylamino-1-aza-3-ethyl-1,3-butadiene, 35 g of 2-chloroacrylonitrile and 112 ml of triethylamine are stirred in 400 ml of acetonitrile for 7 hours at 70° C. The brown reaction mixture is cooled and then filtered and concentrated by evaporation. The residue is dissolved in dioxane and gaseous HCl is introduced. The batch is stirred for 1 hour at room temperature, then concentrated by evaporation, and the residue is partitioned between chloroform and 2N sodium carbonate solution. The organic phase is separated, dried and concentrated by evaporation. The oily residue is distilled under a high vacuum, affording 30.6 g of a yellowish oil with a boiling point of 75°–79° C./3·10$^{-1}$ mbar.

IR (in CHCl$_3$): 2240 cm$^{-1}$ (C≡N).

EXAMPLE 2

Preparation of 5-n-butyl-2-cyanopyridine 0.1 mole of 1-dimethylamino-1-aza-3-n-butyl-1,3-butadiene, 0.1 mole of 2-chloroacrylonitrile and 0.2 mole of triethylamine are heated in 100 ml of acetonitrile for 20 hours to 60° C. The reaction mixture is concentrated by evaporation and the residue is dissolved in dioxane. The solution is filtered and gaseous HCl is introduced. The batch is stirred for 15 minutes at room temperature and then concentrated by evaporation. The residue is partitioned between CH$_2$Cl$_2$ and 1N NaHCO$_3$. The organic phase is dried, concentrated by evaporation and distilled under a high vacuum, affording 10.0 g (63%) of a yellowish oil with a boiling point of 86°–87° C./3·10$^{-1}$ mbar.

EXAMPLE 3

Preparation of 4,5-dimethyl-2-cyanopyridine

The procedure of Example 2 is repeated, using 1-dimethylamino-1-aza-3,4-dimethyl-1,3-butadiene. The residue is distilled under a high vacuum (b.p. 91° C.), affording yellowish crystals with a melting point of 72°–74° C. (digestion in ether/hexane gives colourless crystals).

EXAMPLE 4

Preparation of 5-isopropylpicolinonitrile 83.8 g (0.6 mole) of 1-dimethylamino-1-aza-3-isopropyl-1,3-butadiene and 121.4 g (1.2 moles) of triethylamine are dissolved in 325 ml of acetonitrile. To this solution are added 52.5 g (0.6 mole) of α-chloroacrylonitrile. This solution is heated for 4 hours to 70° C., cooled, filtered, and concentrated by evaporation. The oily residue is dissolved in dioxane and gaseous HCl is introduced into the solution with ice cooling until the pH is 1. After 30 minutes, the batch is concentrated by evaporation and the residue is partitioned between chloroform and 1N NaHCO$_3$. The organic phase is dried and concentrated by evaporation. The residual oil is distilled under a high vacuum at 81°–84° C. The distillate solidifies, affording 60.1 g (68.5%) of the title compound with a melting point of 47°–49° C.

EXAMPLE 5

Preparation of 2-cyano-5-methylpyridine 19.6 g of 1-dimethyl-1-aza-3-methyl-1,3-butadiene, 17.5 g of 2-chloroacrylonitrile and 33.6 g of diazabicyclooctane (DABCO) are heated in 200 ml of acetonitrile for 30 hours to reflux. The reaction mixture is concentrated by evaporation and the residue is slightly acidified with 1N HCl and extracted with chloroform. The organic extract is dried and concentrated by evaporation and the residue is distilled. b.p. (6·10$^{-3}$ bar) 63°–69° C. The distillate is digested with petroleum ether. The title compound is isolated in the form of crystals with a melting point of 72°–74° C.

EXAMPLE 6

Preparation of ethyl 5-methylpyridine-2-carboxylate 6.1 g of triethylamine are added at 0° C. to 13 g of ethyl 2,3-di-bromopropionate in 50 ml of dioxane. The mixture is stirred for 2 hours at room temperature and then a solution of 5.6 g of 1-dimethylamino-1-aza-3-methyl-1,3-butadiene and 6.1 g of triethylamine in 50 ml of dioxane is added dropwise. The reaction mixture is kept for 30 hours at 70° C. and then cooled and concentrated by evaporation. The residue is partitioned between water and ether and the organic phase is washed with brine, dried and concentrated by evaporation. The residue is distilled under reduced pressure, affording 3.2 g of the title compound as an oil with a boiling point of 69°–74° C. (at 0.08 mbar).

EXAMPLE 7

Preparation of 3-cyano-5,6,7,8-tetrahydroisoquinoline 7.6 g cyclohex-1-ene-carboxaldehyde-N,N-dimethylhydrazone, 4.4 g of 2-chloroacrylonitrile and 10.1 g of triethylamine are heated in 75 ml of dioxane for 18 hours to 90° C. The reaction mixture is concentrated by evaporation and the residue is acidified with 1N HCl and extracted three times with chloroform. The combined extracts are dried and concentrated by evaporation and the residue is chromatographed over silica gel. Pale yellow crystals of the title compound are isolated. Melting point: 56°–59° C.

EXAMPLE 8

Preparation of 2-cyano-1,4-dihydro-1-dimethylamino-5-ethylpyridine 12.6 g of 1-dimethylamino-1-aza-3-ethyl-1,3-butadiene, 8 ml of 2-chloroacrylonitrile and 27.8 ml of triethylamine are heated in 40 ml of dioxane for 3½ hours to 70° C. The reaction mixture is concentrated by evaporation and the residue is chromatographed over silica gel with a 16:1 mixture of hexane/ethyl acetate, affording 8.2 g of the title compound as a yellow oil which, on standing at room temperature, spontaneously reacts further to 2-cyano-5-ethylpyridine, with elimination of dimethylamine.

What is claimed is:

1. A process for the preparation of a substituted pyridine of formula I

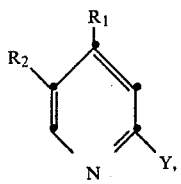

wherein $R_1$ is hydrogen or unsubstituted linear or branched $C_1$–$C_6$alkyl; $R_2$ independently has the same meaning as $R_1$ and is additionally fluorine, chlorine or bromine; or $R_1$ and $R_2$ together are an unsubstituted $C_3$–$C_4$alkylene bridge and Y is CN or COOR$_3$, wherein $R_3$ is $C_1$–$C_3$alkyl cyclopentyl, cyclohexyl, phenyl or benzyl or $C_1$–$C_3$alkyl, cyclopentyl, cyclohexyl, phenyl or benzyl which is substituted by $C_1$–$C_4$alkyl, $C_1$–$C_4$ alkoxy or halogen, which process comprises (a) reacting a hydrazone of formula II

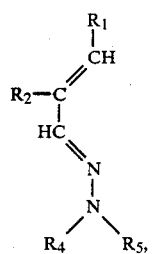

wherein $R_1$ and $R_2$ are as defined for formula I and $R_4$ and $R_5$ are each individually linear or branched $C_1$–$C_6$alkyl, cyclopentyl, cyclohexyl, phenyl, or $C_1$–$C_4$alkylphenyl or, when taken together, are tetramethylene, pentamethylene or 3-oxapentalene, in the presence of an inert solvent and a base, with a compound of formula III

wherein X is chlorine or bromine and Y is as defined for formula I, to give a 1-amino-1,4-dihydropyridine of formula IV

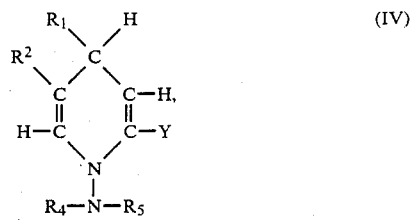

wherein $R_1$, $R_2$, $R_4$, $R_5$ and Y have the given meanings, and (b) converting the compound of formula IV into a compound of formula I by treatment with an acid, with removal of HNR$_4$R$_5$.

2. A process according to claim 1, wherein $R_1$ is hydrogen.

3. A process according to claim 1, wherein $R_2$ is $C_1$–$C_6$alkyl.

4. A process according to claim 1, wherein $R_2$ is ethyl.

5. A process according to claim 1, wherein $R_1$ and $R_2$ together are a tetramethylene group.

6. A process according to claim 1, wherein a polar aprotic solvent is used in reaction step (a).

7. A process according to claim 1, wherein the reaction temperature in reaction step (a) is now lower than 40° C.

8. A process according to claim 1, wherein a base which is soluble in the solvent is used in reaction step (a).

9. A process according to claim 1, wherein the base is a tertiary amine.

10. A process according to claim 1, wherein reaction step (b) is carried out in the presence of a solvent at room temperature.

11. A process according to claim 1, wherein hydrogen chloride is used as acid in reaction step (b).

12. A 1-amino-1,4-dihydropyridine of formula IV

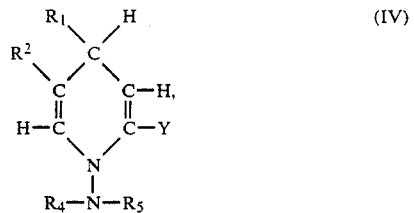

wherein $R_1$ is hydrogen or unsubstituted linear or branched $C_1$–$C_6$alkyl; $R_2$ independently has the same meaning as $R_1$ and is additionally fluorine, chlorine or bromine; or $R_1$ and $R_2$ together are an unsubstituted $C_3$–$C_4$alkylene bridge and Y is CN or COOR$_3$, wherein $R_3$ is $C_1$–$C_3$alkyl cyclopentyl, cyclohexyl, phenyl or benzyl or $C_1-C_3$alkyl, cyclopentyl, cyclohexyl, phenyl or benzyl which is substituted by $C_1-C_4$alkyl, $C_1-C_4$ alkoxy or halogen, and $R_4$ and $R_5$ are each individually linear or branched $C_1-C_6$alkyl, cyclopentyl, cyclohexyl, phenyl, or $C_1-C_4$alkylphenyl or, when taken together, are tetramethylene, pentamethylene or 3-oxapentalene.

* * * * *